US012687466B2

(12) United States Patent
Colburn et al.

(10) Patent No.: US 12,687,466 B2
(45) Date of Patent: Jul. 21, 2026

(54) DEVICES AND METHODS FOR LASER CAPTURE MICRODISSECTION

(71) Applicant: LIFE TECHNOLOGIES CORPORATION, Carlsbad, CA (US)

(72) Inventors: Joel Colburn, Foster City, CA (US); Mousumi Rath; Sarah Ghanbari, Placentia, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 18/771,228

(22) Filed: Jul. 12, 2024

(65) Prior Publication Data

US 2024/0402055 A1     Dec. 5, 2024

Related U.S. Application Data

(63) Continuation of application No. 17/162,034, filed on Jan. 29, 2021, now Pat. No. 12,078,576, which is a
(Continued)

(51) Int. Cl.
*G01N 1/04*          (2006.01)
*B01L 3/00*          (2006.01)
(Continued)

(52) U.S. Cl.
CPC .............. *G01N 1/04* (2013.01); *C12Q 1/6806* (2013.01); *G01N 1/2813* (2013.01); *G01N 1/286* (2013.01);
(Continued)

(58) Field of Classification Search
CPC ........ G01N 1/04; G01N 1/2813; G01N 1/286; G01N 1/34; G01N 2001/028;
(Continued)

(56) References Cited

U.S. PATENT DOCUMENTS

| | | | |
|---|---|---|---|
| 5,632,396 A | 5/1997 | Burns |
| 5,779,074 A | 7/1998 | Burns |

(Continued)

FOREIGN PATENT DOCUMENTS

| | | |
|---|---|---|
| EP | 2395082 A1 | 12/2011 |
| WO | WO-2017027620 A1 | 2/2017 |
| WO | WO-2017027627 A1 | 2/2017 |

OTHER PUBLICATIONS

PCT/US2016/046399, International Search Report and Written Opinion, Nov. 4, 2016, 12 pages.
(Continued)

*Primary Examiner* — Charles Capozzi
*Assistant Examiner* — Jacqueline Brazin

(57) ABSTRACT

A carrier for holding a biological sample includes a substrate. The substrate is configured to engage a first sample chamber comprising a first opening characterized by a first opening diameter or a second sample chamber comprising a second opening characterized by a second opening diameter that is greater than the first opening diameter. The substrate includes an upper portion, a lower portion, and an intermediate portion disposed between the upper portion and the lower portion. The lower portion is disposed below the upper portion and comprises a bottom surface configured to receive a biological sample. The intermediate portion is characterized by a first substrate diameter and the lower portion is characterized by a second substrate diameter that is less than the first substrate diameter.

15 Claims, 5 Drawing Sheets

Related U.S. Application Data continuation of application No. 16/222,933, filed on Dec. 17, 2018, now Pat. No. 10,921,218, which is a continuation of application No. 15/233,756, filed on Aug. 10, 2016, now abandoned.

(60) Provisional application No. 62/341,563, filed on May 25, 2016, provisional application No. 62/303,227, filed on Mar. 3, 2016, provisional application No. 62/203,311, filed on Aug. 10, 2015.

(51) Int. Cl.

| | |
|---|---|
| *C12Q 1/6806* | (2018.01) |
| *G01N 1/02* | (2006.01) |
| *G01N 1/28* | (2006.01) |
| *G01N 1/34* | (2006.01) |

(52) U.S. Cl.
CPC ..... *B01L 3/50825* (2013.01); *B01L 2300/042* (2013.01); *B01L 2300/046* (2013.01); *B01L 2300/0838* (2013.01); *G01N 2001/028* (2013.01); *G01N 2001/045* (2013.01); *G01N 2001/284* (2013.01); *G01N 2001/2886* (2013.01); *G01N 1/34* (2013.01)

(58) Field of Classification Search
CPC ....... G01N 2001/045; G01N 2001/284; G01N 2001/2886; C12Q 1/6806; B01L 3/50825; B01L 2300/042; B01L 2300/046; B01L 2300/0838
USPC .......................................................... 506/2
See application file for complete search history.

(56) References Cited

U.S. PATENT DOCUMENTS

| | | | |
|---|---|---|---|
| 5,859,699 A | | 1/1999 | Baer et al. |
| 5,985,085 A | * | 11/1999 | Baer .................... G01N 1/2813 |
| | | | 156/289 |
| 6,157,446 A | | 12/2000 | Baer et al. |
| 6,469,779 B2 | | 10/2002 | Baer et al. |
| 6,495,195 B2 | | 12/2002 | Baer et al. |
| 6,528,248 B2 | | 3/2003 | Lossing et al. |
| 6,690,470 B1 | | 2/2004 | Baer et al. |
| 6,887,703 B2 | | 5/2005 | Baer et al. |
| 7,049,558 B2 | | 5/2006 | Baer et al. |
| 7,075,640 B2 | | 7/2006 | Baer et al. |
| 7,229,595 B2 | | 6/2007 | Richardson et al. |
| 7,456,938 B2 | | 11/2008 | Malekafzali |
| 7,473,401 B1 | | 1/2009 | Baer |
| 7,556,733 B2 | | 7/2009 | Smith et al. |
| 7,749,388 B2 | | 7/2010 | Pai et al. |
| 7,776,273 B2 | | 8/2010 | Baer et al. |
| 7,964,350 B1 | | 6/2011 | Fekete et al. |
| 8,288,106 B2 | | 10/2012 | Fekete et al. |
| 8,346,483 B2 | | 1/2013 | Kil |
| 8,715,955 B2 | | 5/2014 | Donovan et al. |
| 8,722,357 B2 | | 5/2014 | Baer et al. |
| 8,828,664 B2 | | 9/2014 | Fekete et al. |
| 9,279,152 B2 | | 3/2016 | Fekete et al. |
| 2001/0038449 A1 | | 11/2001 | Baer et al. |
| 2002/0001837 A1 | * | 1/2002 | Baer ....................... G01N 1/40 |
| | | | 435/283.1 |
| 2003/0069413 A1 | | 4/2003 | Pai et al. |
| 2004/0072305 A1 | | 4/2004 | Erlander et al. |
| 2004/0161788 A1 | | 8/2004 | Chen et al. |
| 2005/0239068 A1 | | 10/2005 | Bosnes |
| 2008/0199929 A1 | | 8/2008 | Yeung |
| 2012/0258451 A1 | | 10/2012 | Klimanskaya |
| 2013/0030165 A1 | | 1/2013 | Fabis et al. |
| 2015/0050653 A1 | | 2/2015 | Fekete et al. |
| 2017/0045421 A1 | | 2/2017 | Colburn et al. |
| 2017/0045428 A1 | | 2/2017 | Rath et al. |

OTHER PUBLICATIONS

PCT/US2016/046410, International Search Report and Written Opinion, Nov. 16, 2016, 13 pages.
Sigma Catalog, Biochemical and Reagents for Life Science Research, 2002, p. 2362.

* cited by examiner

DEVICES AND METHODS FOR LASER CAPTURE MICRODISSECTION

CROSS-REFERENCE TO RELATED APPLICATIONS

This application is a continuation application of U.S. patent application Ser. No. 17/162,034, filed on Jan. 29, 2021. U.S. patent application Ser. No. 17/162,034 is a continuation application of U.S. patent application Ser. No. 16/222,933, filed on Dec. 17, 2018, now U.S. Pat. No. 10,921,218. U.S. patent application Ser. No. 16/222,933 is a continuation application of U.S. patent application Ser. No. 15/233,756, filed on Aug. 10, 2016. U.S. patent application Ser. No. 15/233,756 claims the benefit of priority of U.S. Provisional Patent Application No. 62/203,311, filed on Aug. 10, 2015, U.S. Provisional Patent Application No. 62/303,227, filed on Mar. 3, 2016, and U.S. Provisional Patent Application No. 62/341,563, filed on May 25, 2016. All applications named in this section are incorporated herein by reference, each in its entirety.

BACKGROUND OF THE INVENTION

Field of the Invention

The present invention relates generally to methods, devices, and systems for conducting a biological process and more specifically to methods, devices, and systems for conducting a biological process that involve at least one laser capture microdissection process.

Description of the Related Art

Laser capture microdissection (LCM) is a process for obtaining, selecting, and preparing biological samples for further processing or analysis, for example, for conducting at least one of a real-time polymerase chain reaction assay or process, a digital polymerase chain reaction assay or process, a sequencing assay or process, or a next generation sequencing assay or process. There exists a need to provide LCM processes on a variety of types of biological samples having differing processing requirements. Embodiments of the present invention have been found to provide greater flexibility in meeting these needs. Embodiments of the present invention also provide methods, devices, and systems that reduce or eliminate the need for transferring a sample to multiple sample chambers, vials, or tubes in preparation for use in other instruments.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 4 is a side view of the sample carrier in FIG. 1 being attached to a smaller sample chamber or tube.

FIG. 5 is a side view of the sample carrier in FIG. 1 being attached to a larger sample chamber or tube.

DETAILED DESCRIPTION OF THE DRAWINGS

Figure 1:
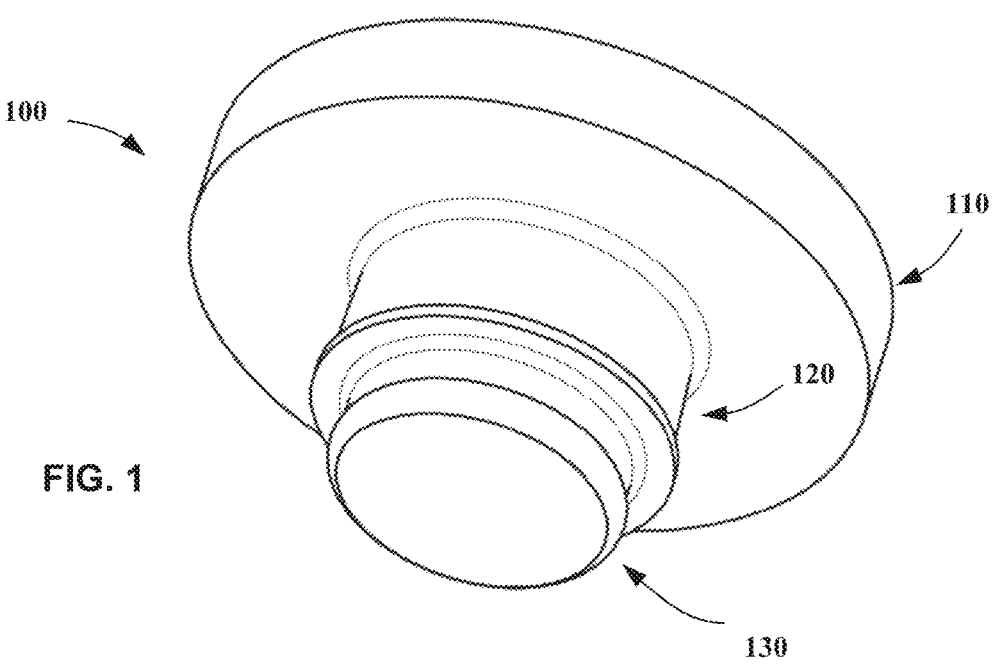
FIG. 1 is a perspective view of sample carrier according to an embodiment of the present invention.
Figure 2:
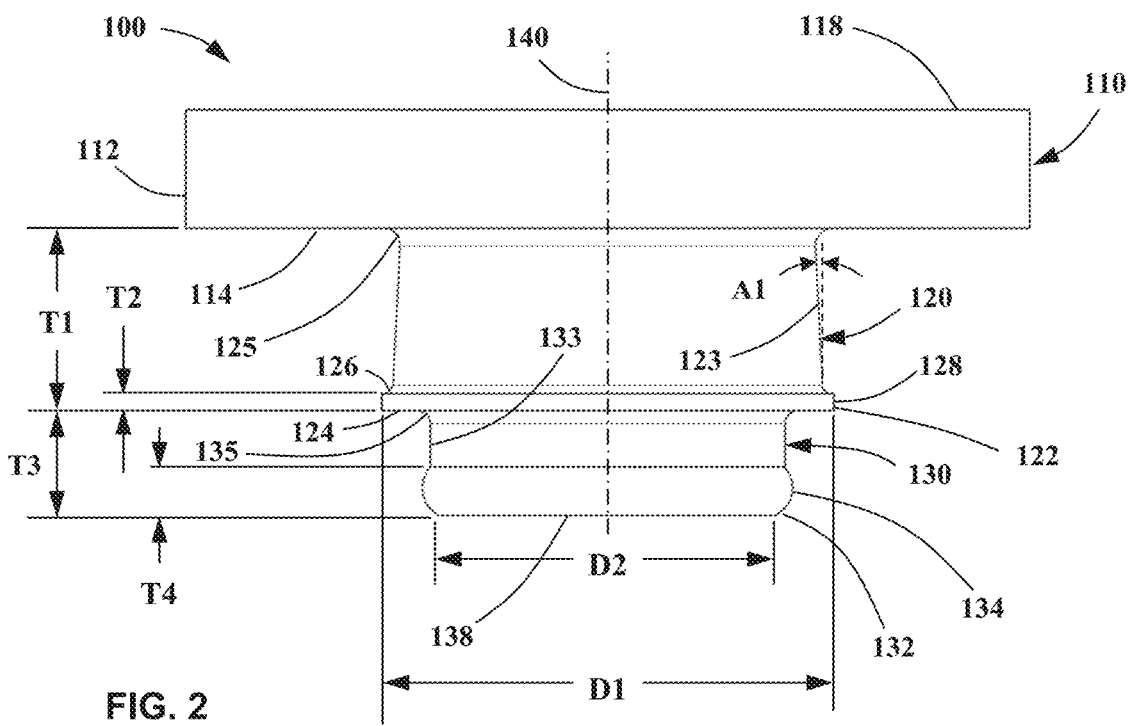
FIG. 2 is a side view of the sample carrier shown in FIG. 1.

Referring to FIGS. 1 and 2, a carrier, holder, or sample carrier 100 according to embodiments of the presentation is configured for holding a biological sample and/or for performing one or more processes on the biological sample. In certain embodiments, sample carrier 100 comprises a substrate comprising a first or upper portion 110 disposed along an axis 140, a second or lower portion 130 disposed along axis 140 and below upper portion 110, and a third or intermediate portion 120 disposed between upper portion 110 and lower portion 130. As used herein in reference to sample carrier 100, the terms "upper", "lower", "above", and "below" refer to sample carrier 100 when orientated as in FIGS. 1 and 2. The use of these terms does not in any way preclude the manufacture or use of sample carrier 100 in orientations different from that shown in FIGS. 1 and 2, for example, in an inverted orientation from that shown in FIGS. 1 and 2. In certain embodiments, sample carrier 100 is configured to accommodate or hold one or more tissue samples or other biological samples for use in a laser capture microdissection (LCM) system. Embodiments of sample carrier 100 may be used in conjunction with systems, methods, devices, and apparatuses disclosed in United States Patent Numbers U.S. Pat. Nos. 5,859,699, 6,157,446, 6,469,779, 6,495,195, 6,528,248, 6,690,470, 6,887,703, 7,049,558, 7,075,640, 7,229,595, 7,456,938, 7,473,401, 7,556,733, 7,749,388, 7,776,273, 8,346,483, 8,715,955, 8,722,357. In addition, embodiments of sample carrier 100 may be used in conjunction with systems, methods, devices, and apparatuses disclosed in U.S. Provisional Patent Application Nos. 62/303,227 and 62/341,563, both of which are herein incorporated by reference in their entirety as if fully set forth herein.

In some embodiments, upper portion 110 comprises an outer perimeter 112, a shoulder 114, and a top surface 118. Upper portion 110 may be configured to facilitate handling and/or stability of sample carrier 100 during use.

In certain embodiments, intermediate portion 120 comprises an outer perimeter 122 characterized by a diameter D1, an adjacent area or side wall 123, and an optional shoulder 124. Intermediate portion 120 may also be characterized by a thickness T1. In some embodiments, intermediate portion 120 may also include one or more of (1) a chamfer, radius, or flare 125, (2) a chamfer, radius, or flare 126, and/or (3) a seating area 128 characterized by a thickness T2 along the axis 140 that may be less than the thickness T1. In some embodiments, the side wall 123 and/or a wall of the seating area 128 are parallel to the axis 140. Alternatively, it has been discovered that side wall 123 may be advantageously tapered inwardly by an angle A1.

In certain embodiments, lower portion 130 comprises an outer perimeter 132 characterized by a diameter D2, an adjacent area or side wall 133, and a bottom surface 138. The outer perimeter 132 is characterized by a diameter D2 that is less than D1. The lower portion 130 may also include one or more of a chamfer, radius, or flare 135 or a seating area 134 characterized by a thickness T4 along the axis 140 that is less than the thickness T1. Bottom surface 138 is configured to receive one or more biological samples, for example, one or more tissue samples. The biological sample may be attached to bottom surface 138, for example, in preparation for a laser capture microdissection process.

Figure 3:
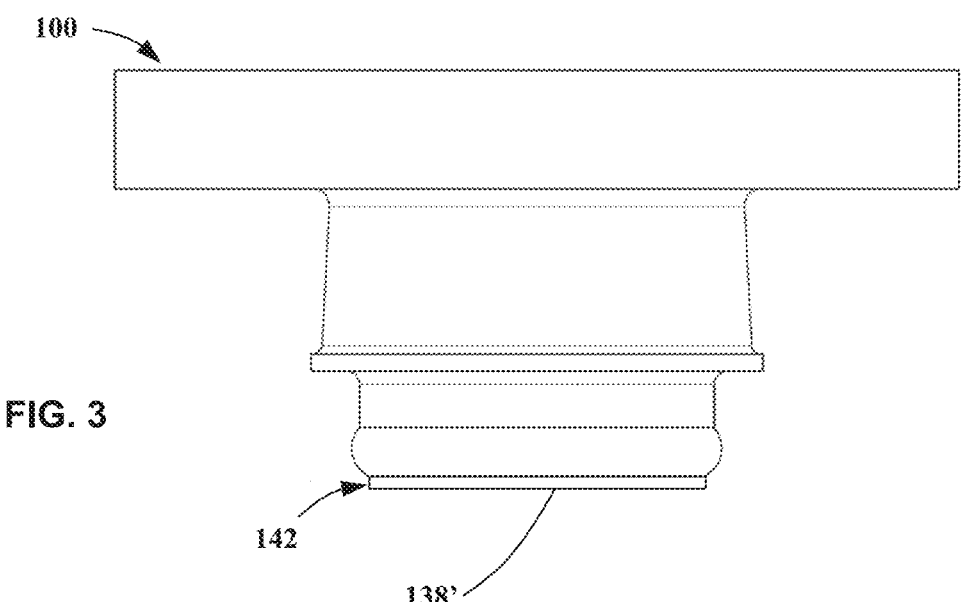
FIG. 3 is a side view of a sample carrier according to another embodiment of the present invention.

Referring additionally to FIG. 3, sample carrier 100 may further comprise and/or be configured to accommodate a transfer film 142 that may be used accommodate or hold a biological sample in an LCM process. LCM transfer film 142 may be applied to bottom surface 138 by punching a circular section from a sheet of ethylene vinyl acetate or other suitable material. Alternatively, the LCM transfer film 142 may be molded to the bottom of the sample carrier 100. The LCM transfer film 142 may be deposited on bottom surface 138 to form a new bottom surface 138' using a process such as spin coating, dipping, or spraying, or by adhering a pre-made file onto the cap by baking at specific conditions. In some embodiments, the LCM transfer film 142 contains a dye capable of absorbing laser energy from the LCM instrument.

Figures 4, 5:
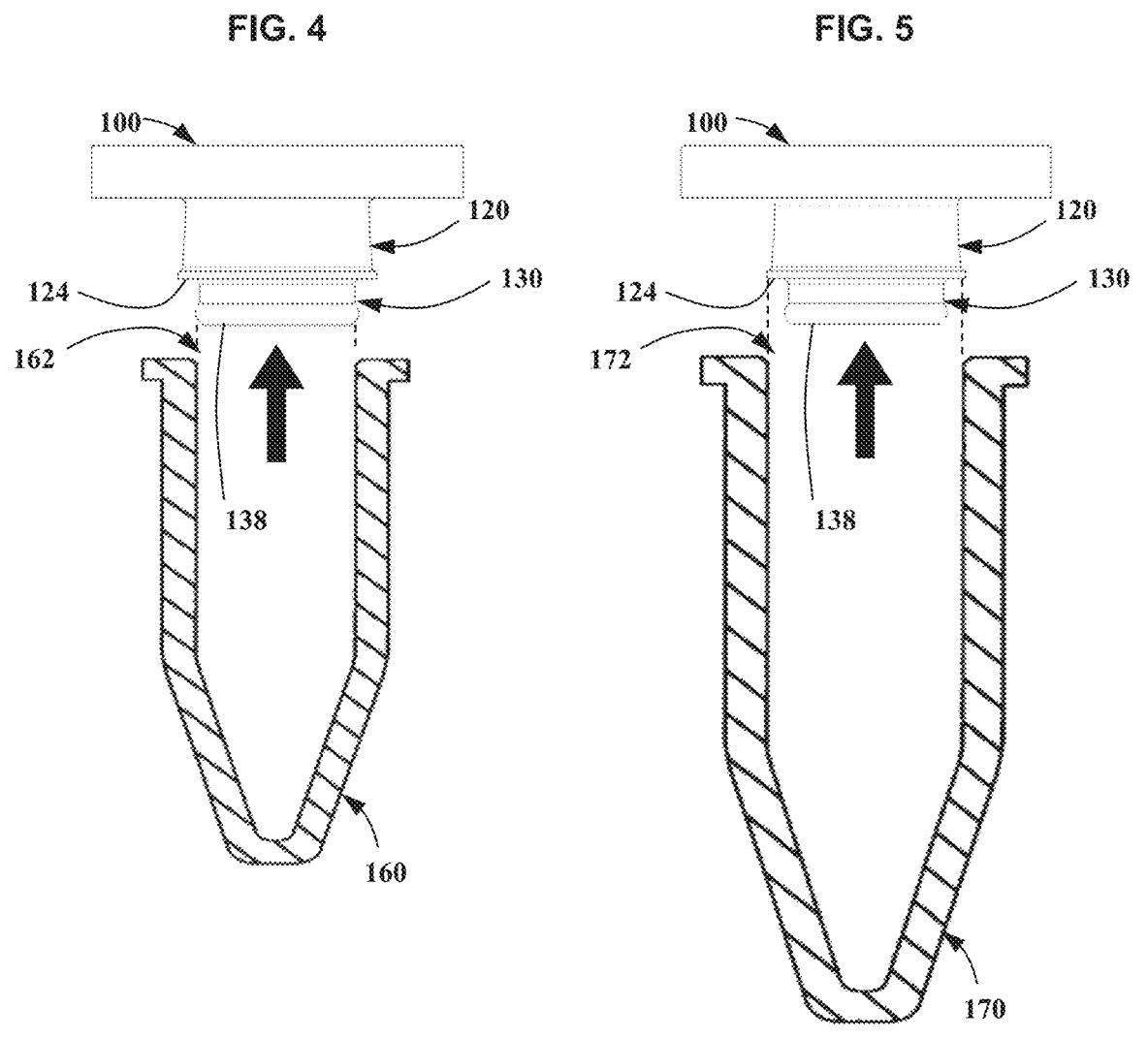

Referring to FIGS. 4 and 5, in certain embodiments, sample carrier 100 may be configured to accommodate, receive, be compatible with, and/or fit into two or more different sized chambers, vessels, wells, or tubes, for example, in two or more different sized collection, processing, or collection, extraction, or reaction tubes or wells. Suitable chambers, vessels, wells, or tubes include, but are not limited to, those disclosed in U.S. Pat. Nos. 5,859,699, 7,075,640, 6,157,446, 7,473,401, 7,556,733, 7,776,273. For example, as shown in the illustrated embodiments, sample carrier 100 may be part of a system or kit comprising sample carrier 100 and one or more of a sample collection, processing, or reaction tube(s), well(s), or chamber(s) 160 and/or a sample collection, processing, or reaction tube(s), wells(s), or chamber(s) 170. Chamber 160 comprises an opening or interface 162 that is configured to enclose bottom surface 138 and to fit into, or be attached to, lower portion 130 of sample carrier 110. Chamber 170 comprises an opening or interface 172 that is configured to enclose bottom surface 138 and shoulder 124. Chamber 170 is configured to fit into, or be attached to, intermediate portion 120 of sample carrier 110.

In certain embodiments, chamber 170 has a volume or capacity of 0.5 milliliters or about 0.5 milliliters in order to accommodate applications where larger biological or tissue capture sizes are desired or necessary (e.g., greater than or equal to 2000 micron). In such embodiments, a user may need a higher lysis volume in order to achieve efficient lysis. Using a low lysis volume in such circumstances for large capture size may make the sample tissue homogenate more viscous and be more difficult to pipette, resulting in low nucleic acid yield. Therefore, for a relatively large capture size may be used to achieve better lysis under these conditions. A user thus has the option to use larger lysis volume and, for example, purify RNA in the sample using filter column to concentrate nucleic acid yield with a prescribed column binding strategy and elute at a smaller volume. Suitable filter columns include, but are not limited to, those disclosed in U.S. Pat. Nos. 7,229,595, 7,749,388, and/or 7,556,733. Embodiments of sample carrier 100 provide flexibility to fit into 0.5 mL tube.

Figure 6:
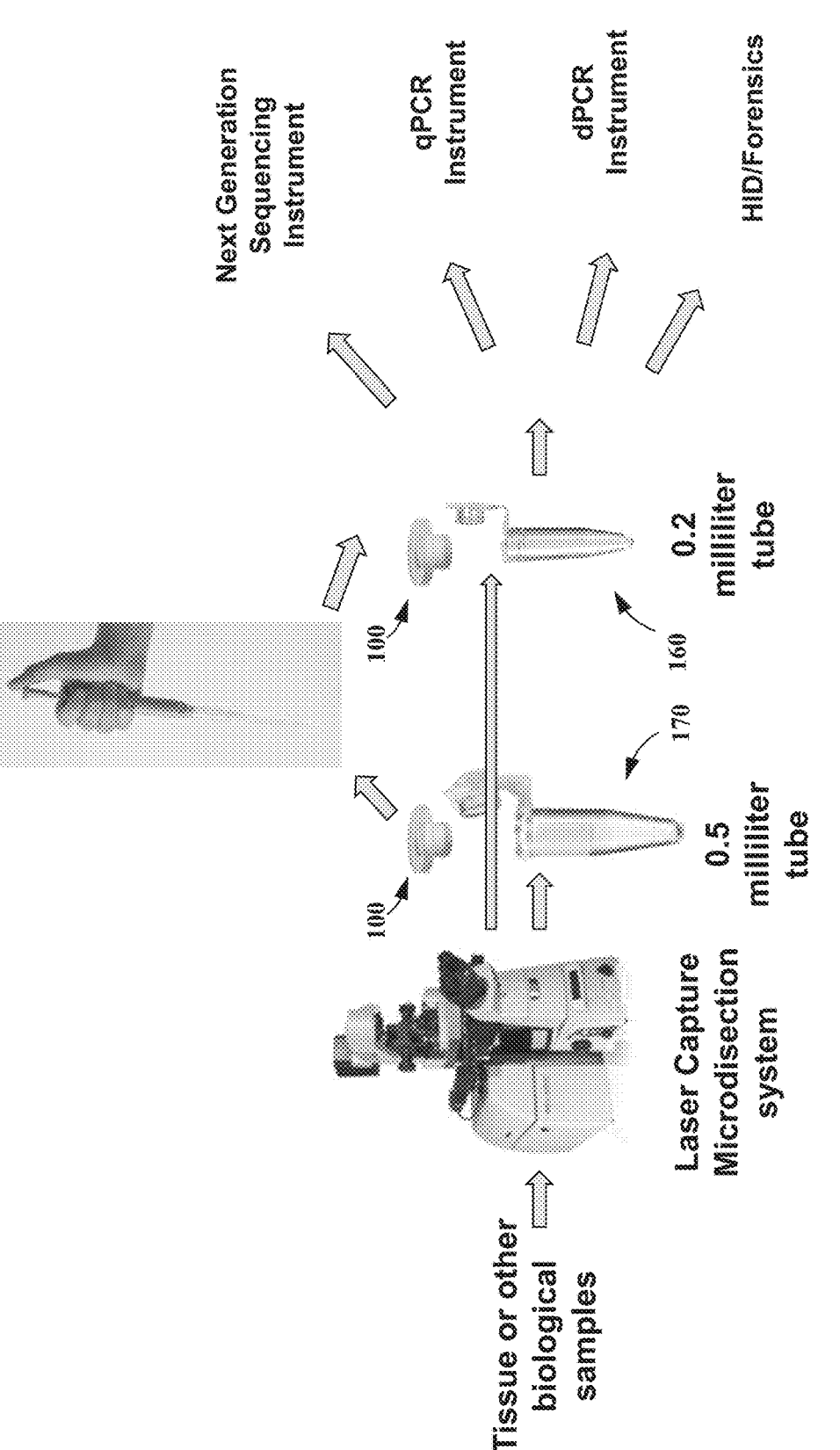
FIG. 6 is a schematic view of processes according to embodiments of the present invention.
Figure 7:
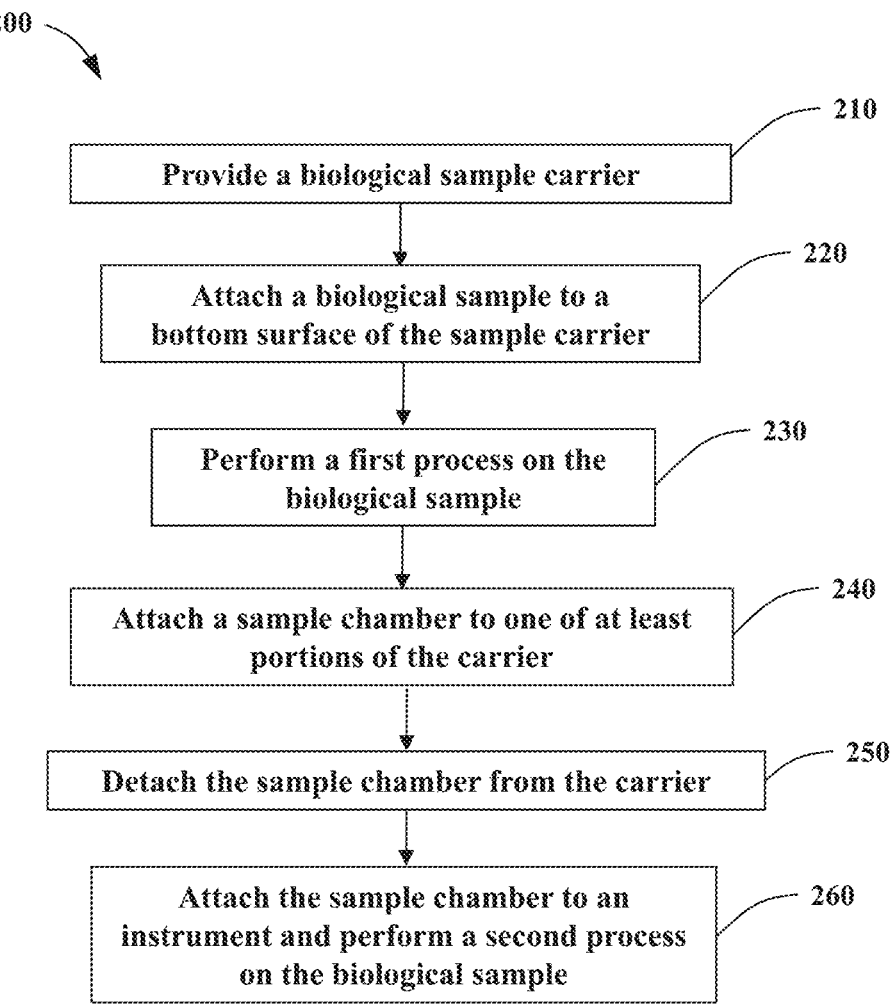
FIG. 7 is a flow diagram of method according to embodiments of the present invention.

Additionally or alternatively, chamber 160 may be configured with a 0.2 milliliter volume and used in combination with a filter column and transfer into larger sample processing chambers, for example, for reducing the number of washing steps in a process. In such embodiments, an extraction step may be performed by transferring a lysate to a filter column. Thus, embodiments of the present invention offer a user the advantage of flexibility in the size tube or chamber used between LCM and processing using a filter column. Advantageously, embodiments of the present invention may be used with filter columns also accommodating different size reaction tubes, such as those disclosed in U.S. Pat. Nos. 7,229,595, 7,749,388, and 7,556,733. In certain embodiments, reaction tubes having 0.2 milliliter, 0.5 milliliter, 1.5 milliliter, and/or 2.0 milliliter volumes or capacities may be used in combination with sample carrier 100 and a filter column according to one of the previously cited patents, thus offering a user enhanced flexibility in processing of a sample in preparation for further analysis, for example, analysis in an instrument for performing an assay or process for RT, qPCR, dPCR, sequencing, next generation sequencing (NGS), or the like. FIG. 6 illustrates in the lower path thereof the advantages of using a smaller sample chamber or tube for transferring the sample between a LCM process and another process without the need for intermediate transfer into another sample chamber or tube.

In other embodiments, it is desirable or necessary in an application, process, assay, or experiment to proceed directly from lysis to another process such as RT, qPCR, dPCR, NGS, or the like. This may be the situation for applications having low input samples (e.g., single to few cells from tumor tissue, liquid biopsy samples, or the like). In such situations, reducing or eliminating transfer of samples between different sample tube may be desirable, since such transfers may lead to undesirable contamination of the sample(s). The downstream for such applications need smaller sample input volume. Embodiments of sample carrier 100 designs the flexibility to fit into 0.2 milliliter tube mitigates issues in the prior art and provide workflow case, flexibility, and sensitivity to a user. A user may capture a single or few cells or smaller capture size on sample carrier 100, lyse the cells in 10 ul lysate volume in 0.2 milliliter tube, and perform RT, amplification, or sequencing protocols, process, or assays using the same 0.2 mL tube. Advantageously, a 10 microliter lysate volume is compatible with existing single cells to Ct protocols, as well as NGS RT step with Thermo Fisher Scientific's Superscript VILO kit used in Thermo Fisher Scientific's AmpliseqRNA library workflow.

In certain embodiments, opening 162 of chamber 160 is characterized by a diameter that is equal to, or about equal to, the diameter D2 of sample carrier 100, while attachment area 172 of tube 170 is characterized by a larger diameter that is equal to or about equal to D1 of sample carrier 100. In such embodiments, lower portion 130 is configured to accommodate, receive, be compatible with, and/or fit into chamber 160 at opening 162, while intermediate portion 120 is configured to accommodate, receive, be compatible with, and/or fit into chamber 170 at opening 172. In the illustrated embodiments of FIGS. 4 and 5, chamber 170 has a volume or capacity that is greater than that of chamber 160. Alternatively, chamber 170 may have the same, or approximately the same, volume as chamber 160. In certain embodiments, chamber 160 may have a volume or capacity of 0.2 milliliters or about 0.2 milliliters and chamber 170 may have a volume or capacity of 0.5 milliliters or about 0.5 milliliters. In certain embodiments, chamber 160 may have a volume of less than 0.2 milliliters, for example, less than or equal to 0.1 milliliters, less than or equal to 50 microliters, less than or equal to 20 microliters. In certain embodiments, chamber 170 may have a volume that is greater than 0.5 milliliters, for example, chamber 170 may have a volume that is greater than or equal to 1.5 milliliters or greater than or equal to 2 milliliters, for example, to accommodate use with processing using a filter column.

Various features in the vicinity of bottom surface 138 and/or shoulder 124 may be used to improve the ability of sample carrier 100 to suitably interface with and/or to hold or maintain chambers 160, 170 during storage and/or use. For example, in certain embodiments, the diameter of opening 162 is less than D2 and/or the diameter of opening 172 is less than D1. Such dimensioning of opening 162 and/or opening 172 may be configured to provide an interference fit the corresponding chamber 160, 170 and sample carrier 100.

In certain embodiments, seating area 128 of intermediate portion 120 may have a diameter that is greater than the diameter of opening 172 of chamber 170 and/or that is less than a diameter of intermediate portion 120 adjacent to or above seating area 128. Additionally or alternatively, side wall 123 of intermediate portion 120 may be sloped by angle A1. It has been discovered that such a sloped wall configuration aids in maintaining chamber 170 onto sample carrier 100 during use, for example, by allowing a certain amount of misalignment between sample carrier 100 and chamber 170. In certain embodiments, slope angle A1 is at least 2 degrees, for example, between 2 and 3 degrees (e.g., about 2.5 degrees or about 2.6 degrees). In other embodiments, slope angle A1 is at least 3 degrees or at least 4 degrees. The value of the angle A1 may be selected based parameters including one or more of the diameter of D1, the diameter of D2, the length or shape of chamber 170, the weight of chamber 170, the degree of sealing necessary or desired between chamber 170 and sample carrier 100, or the like. In certain embodiments, a wall of lower portion 130 may be sloped in a way equal or similar to that describe for intermediate portion 120.

In certain embodiments, seating area 134 of lower portion 130 is characterized by thickness T4 along the axis 140, where seating area 134 is characterized by a diameter that is greater than D2 and/or a diameter of portions of the wall of lower portion 130 that are adjacent to or above seating area 134. Seating area 134 may comprise an arcuate or curved surface or profile, for example, as shown in FIG. 2. For example, it has been found that seating area 134 may have a radius of curvature of about 0.018 inches in order to maintain a sufficient amount of engagement during use between chamber 160 and lower portion 130 of sample carrier 100. In certain embodiments, seating area 134 comprises at least one of an O-ring, a seal, or a sealing material. It has been discovered that such features of seating area 134 may aid in maintaining chamber 160 onto sample carrier 100 during use, for example, by allowing a certain amount of misalignment between sample carrier 100 and chamber 160. In certain embodiments, one or more features of seating area 134 of lower portion 130 may be incorporated into seating area 128 of intermediate portion 120.

In certain embodiments, the thickness T1 has been found to be critical in maintaining engagement during use between chamber 170 and intermediate portion 120 of sample carrier 100. For example, for an intermediate portion 120 diameter D1 of 0.266 inches to 0.270 inches, it has been found that a thick T1 of at least 0.065 inches maintains a sufficient amount of engagement during use between chamber 170 and intermediate portion 120 of sample carrier 100. In certain embodiments, the thickness T3 has been found to be critical in maintaining engagement during use between chamber 160 and lower portion 130 of sample carrier 100. For example, for lower portion 120 diameter D2 of 0.199 inches to 0.201 inches, it has been found that a thick T2 of at least 0.100 inches maintains a sufficient amount of engagement during use between chamber 160 and lower portion 130 of sample carrier 100.

Either chamber 160, 170 may subsequently be used in biological process or assay using a selected instruments (e.g., a next generation sequencing instrument, a qPCR instrument, a dPCR instrument, or an instrument for HID/ Forensics). In certain embodiments, the selected sample in chamber 170 may be further processed prior to use in the selected instrument.

In certain embodiments, a method 200 of processing a biological sample comprises an element 210 of providing a sample carrier 100 according to an embodiment of the present invention. Method 200 also comprises an element 220 of attaching a biological sample to a bottom surface of sample carrier 100. Method 200 further comprises an element 230 of performing a first process on the biological sample. Method 200 additionally comprises an element 240 of attaching a sample chamber (e.g., sample chamber 160 or sample chamber 170) to a portion of sample carrier 100 (e.g., to intermediate portion 120 or lower portion 130 of sample carrier 100) and an element 250 of detaching the sample chamber from the carrier. Method 200 further comprises an element 260 of attaching the sample chamber to an instrument and performing a second process on the biological sample.

The first biological process may comprise a laser capture microdissection process. The second process may comprise one or more of a real-time polymerase chain reaction assay or process, a digital polymerase chain reaction assay or process, an RT assay or process, a sequencing assay or process, or a next generation sequencing assay or process.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

The following United States Patents are all herein incorporated by reference in their entirety:
U.S. Pat. No. 5,859,699;
U.S. Pat. No. 6,157,446;
U.S. Pat. No. 6,469,779;
U.S. Pat. No. 6,495,195;
U.S. Pat. No. 6,528,248;
U.S. Pat. No. 6,690,470;
U.S. Pat. No. 6,887,703;
U.S. Pat. No. 7,049,558;
U.S. Pat. No. 7,075,640;
U.S. Pat. No. 7,229,595;
U.S. Pat. No. 7,456,938;
U.S. Pat. No. 7,473,401;
U.S. Pat. No. 7,556,733;
U.S. Pat. No. 7,749,388;
U.S. Pat. No. 7,776,273;
U.S. Pat. No. 7,964,350;
U.S. Pat. No. 8,288,106;
U.S. Pat. No. 8,346,483;
U.S. Pat. No. 8,715,955;
U.S. Pat. Nos. 8,722,357; 8,828,664;
U.S. Pat. No. 9,279,152.

What is claimed:

1. A system for a biological process, comprising:

(a) a sample carrier, comprising:

a cap formed from a substrate with an upper portion of the substrate comprising an outer perimeter, a first shoulder, and the top surface; an intermediate portion of the substrate, wherein the intermediate portion comprises a first seating area with a first diameter and a second shoulder; a lower portion of the substrate, wherein the lower portion comprises a second seating area with a second diameter; and a bottom surface; wherein the outer perimeter of the upper portion is larger than the first diameter of the first seating area of the intermediate portion, and wherein the first diameter is larger than the second diameter of the second seating area of the lower portion; and wherein a sample transfer film is applied to the bottom surface of the cap; and (b) two or more sample chambers, at least one selected from each of:

(i) a first sample chamber comprising a first opening characterized by a first opening diameter; and (ii) a second sample chamber comprising a second opening characterized by a second opening diameter that is less than the first opening diameter;

wherein the first seating area of the intermediate portion of the sample carrier is configured to engage the first opening of the first sample chamber and the second seating area of the lower portion of the sample carrier is configured to engage the second opening of the second sample chamber; and wherein the cap is either disengaged from both the first sample chamber and the second sample chamber, or the cap is engaged with the first sample chamber, or the cap is engaged with the second sample chamber.

2. The system of claim 1, wherein the first sample chamber has a total capacity of 0.5 milliliters.

3. The system of claim 1, wherein the second sample chamber has a total capacity of 0.2 milliliters.

4. The system of claim 1, wherein the intermediate portion of the sample carrier comprises a first seating area with a first diameter configured to provide an interference fit within the first sample chamber opening.

5. The system of claim 1, wherein the lower portion of the sample carrier comprises a second seating area with a second diameter configured to provide an interference fit within the second sample chamber opening.

6. A method of performing at least two biological processes, comprising:

providing a system according to claim 1;

performing a first biological process to attach a sample to the sample transfer film applied to the bottom surface of the sample carrier;

attaching a sample chamber to either the intermediate portion or the lower portion of the sample carrier;

extracting the sample from the sample transfer film; and performing a second biological process on the sample.

7. The method of claim 6, wherein the first biological process is a laser capture microdissection.

8. The method of claim 6, wherein the first biological process is a laser capture microdissection and the second biological process is a polymerase chain reaction assay or process.

9. The method of claim 6, wherein the first biological process is a laser capture microdissection and the second biological process is either a real-time or digital polymerase chain reaction assay or process.

10. The method of claim 6, wherein the first biological process is a laser capture microdissection and the second biological process is a reverse transcriptase assay or process.

11. The method of claim 6, wherein the first biological process is a laser capture microdissection and the second biological process is a sequencing assay or process.

12. The method of claim 6, wherein the first biological process is a laser capture microdissection and the second biological process is a next generation sequencing assay or process.

13. The method of claim 8, further comprising a sequencing assay or process.

14. The method of claim 10, further comprising a sequencing assay or process.

15. The method of claim 10, further comprising a polymerase chain reaction assay or process and a sequencing assay or process.

* * * * *